(12) United States Patent
Ciuhu et al.

(10) Patent No.: US 10,398,507 B2
(45) Date of Patent: Sep. 3, 2019

(54) METHOD FOR SETTING A CUTTING DISTANCE BETWEEN A LASER BEAM AND A SKIN SURFACE IN A LASER SHAVING DEVICE

(71) Applicant: KONINKLIJKE PHILIPS N.V., Eindhoven (NL)

(72) Inventors: Calina Ciuhu, Eindhoven (NL); Bastiaan Wilhelmus Maria Moeskops, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 157 days.

(21) Appl. No.: 15/565,796

(22) PCT Filed: Apr. 12, 2016

(86) PCT No.: PCT/EP2016/057949
§ 371 (c)(1),
(2) Date: Oct. 11, 2017

(87) PCT Pub. No.: WO2016/166068
PCT Pub. Date: Oct. 20, 2016

(65) Prior Publication Data
US 2018/0116719 A1    May 3, 2018

(30) Foreign Application Priority Data
Apr. 14, 2015   (EP) ..................... 15163594

(51) Int. Cl.
*A61B 18/20* (2006.01)
*A61B 18/00* (2006.01)
*A61B 90/00* (2016.01)

(52) U.S. Cl.
CPC .. *A61B 18/203* (2013.01); *A61B 2018/00452* (2013.01); *A61B 2018/00642* (2013.01); *A61B 2090/033* (2016.02)

(58) Field of Classification Search
CPC ............ A61B 18/203; A61B 2090/033; A61B 2018/2035; A61B 2090/036;
(Continued)

(56) References Cited

U.S. PATENT DOCUMENTS 8,529,560 B2    9/2013   Ferren

FOREIGN PATENT DOCUMENTS

EP     2189129 A1    5/2010
EP     2656982 A1   10/2013
(Continued)

*Primary Examiner* — Aaron F Roane

(57) ABSTRACT

The present application relates to a method for setting a cutting distance ($\delta_{laser_{13}skin_{13}opt}(z)$) between a laser beam (14) and a skin surface (5) in a laser shaving device (1), said laser shaving device having a laser deactivation threshold ($\delta_{laser\_skin\_opt}(z)$), said method comprising: operating an optical system (12) to generate the laser beam; determining a skin variation value ($\sigma$) indicative of the variation in the distance of the skin surface from a reference point; determining a cutting distance between said laser beam and the skin surface in dependence on at least the laser deactivation threshold and said skin variation value; and adjusting said optical system to locate the laser beam in dependence on said determined cutting distance. Determining the said skin variation value comprises the steps of generating information indicative of an ideal skin surface ($\bar{Y}_{skin}(z)$) and the distances from said ideal skin surface that said skin surface is; and determining a standard deviation of said skin surface distance from said ideal skin surface.

10 Claims, 2 Drawing Sheets

(58) Field of Classification Search
CPC ........... A61B 2018/00452; A61B 2018/00476; A61B 2018/00642; A61B 2018/00666; A61B 2018/00702
USPC .......................................................... 606/9
See application file for complete search history.

(56) References Cited

FOREIGN PATENT DOCUMENTS

| | | | |
|---|---|---|---|
| GB | 2495248 | A | 4/2013 |
| WO | 9533600 | A1 | 12/1995 |
| WO | 2013160798 | A1 | 10/2013 |
| WO | 2014020512 | A1 | 2/2014 |
| WO | 2014139968 | A1 | 9/2014 |

METHOD FOR SETTING A CUTTING DISTANCE BETWEEN A LASER BEAM AND A SKIN SURFACE IN A LASER SHAVING DEVICE

This application is the U.S. National Phase application under 35 U.S.C. § 371 of International Application No. PCT/EP2016/057949, filed on Apr. 12, 2016, which claims the benefit of International Application No. 15163594.3 filed on Apr. 14, 2015. These applications are hereby incorporated by reference herein.

FIELD OF THE INVENTION

The present invention relates to a method for setting a cutting distance between a laser beam and a skin surface in a laser shaving device.

BACKGROUND OF THE INVENTION

It is known to use a laser beam to sever hair as an alternative to an arrangement of mechanical blades. Hair exposed to a laser beam will absorb energy from the laser beam and the hair will either be severed by vaporisation or by laser induced optical breakdown and a resulting shockwave. The laser beam does not require a moving cutting part to be placed against the skin or hair and so the problem of cutting elements becoming blunt is eliminated.

It is known that laser beams can cause damage and irritation to the user if the high intensity laser beam contacts the skin. It is also known to deactivate the laser beam when the skin is too close to the laser beam to avoid such damage and irritation being caused. However, the closest shave is achieved by keeping the distance between the laser beam and the skin surface to a minimum. This results in the laser beam being deactivated frequently. Deactivation of the laser beam when the skin is in the vicinity of the laser beam also results in hairs not being cut. Therefore, the number of strokes it takes for a user to achieve the desired closeness is too large to be acceptable for a normal shaving ritual or the length of the user's stubble is too long.

Patent application WO 2014/139968 A1 discloses a device for cutting hair wherein a laser beam is used to sever hairs, the laser beam being parallel to and spaced from the skin. The device according to WO 2014/139968 A1 is provided with a laser positioning mechanism which is arranged such that, during use, a distance between the laser beam and the is changed to maintain a predetermined distance.

SUMMARY OF THE INVENTION

It is an object of the invention to provide a laser shaving device which substantially alleviates or overcomes the problems mentioned above.

According to the present invention, there is provided a method for setting a cutting distance between a laser beam and a skin surface in a laser shaving device, said laser shaving device having a laser deactivation threshold, said method comprising: operating an optical system to generate the laser beam; determining a skin variation value indicative of the variation in distance of the skin surface from a reference point; determining a cutting distance between said laser beam and said skin variation value; and adjusting said optical system to locate the laser beam in dependence on said determined cutting distance.

With this method, the laser shaving device can be set up to give the closest shave possible in a certain number of shaving strokes dependent on the skin variation and the intensity of the laser beam.

Determining said skin variation value comprises: generating information indicative of an ideal skin surface and the distances from said ideal skin surface that said skin surface is; and determining a standard deviation of said skin surface distance from said ideal skin surface.

Therefore, the condition of the skin surface can be constantly monitored.

Determining said skin variation value may further comprise: selecting a desired laser activation percentage during a shaving stroke corresponding to a shaving condition; and determining the corresponding percentage of said standard deviation that the skin variation distance must be in order to achieve said desired laser activation percentage.

Therefore, the laser beam can be positioned relative to the ideal skin surface at the cutting distance which will achieve the closest shave possible in a given number of strokes.

Determining said laser beam deactivation threshold may comprise generating information indicative of an allowable intensity radius of the laser beam and a safety margin distance.

The method for setting a cutting distance between a laser beam and a skin surface in a laser shaving device may further comprise: generating information indicative of the distance between said laser beam and said skin surface; and ceasing generation of the laser beam when the skin surface has exceeded said laser beam deactivation threshold.

Therefore, irritation of the skin surface is avoided by turning the laser beam off when the skin surface gets too close to it.

The optical system may adjust said laser beam to be at said cutting distance, which is the sum of said laser beam deactivation threshold plus a skin variation distance, which is dependent on said skin variation value, from said skin surface.

Therefore, the method can be used to set the cutting distance to accommodate different types of skin surface. The laser shaving device may also react to changes in the skin surface.

The skin variation distance is increased to reduce the number of shaving strokes needed to shave a beard and decreased to improve the closeness of the shave.

Therefore, the method of setting the cutting distance can be used to determine the cutting distance for various types of shaving conditions. Therefore, the method can be used to set the distance for numerous shaving rituals consisting of only a few strokes or of many and yield the closest shave for each one.

The method for setting a cutting distance between a laser beam and a skin surface in a laser shaving device may further comprise: selecting a desired shaving condition using a user input; and adjusting said optical system to position said laser beam at the corresponding cutting distance from said skin surface.

Therefore, the user is able to decide his stubble length by choosing the corresponding shaving ritual that he wishes to perform. Using the method, multiple shaving rituals may be performed with the same laser shaving device.

The optical system may adjust said laser beam to said cutting distance which is greater than 50 μm and less than 300 μm.

Therefore, the laser shaving device is able to reduce the length of the hair by at least 80 μm in one stroke.

The optical system may adjust said laser beam to said cutting distance which is greater than 100 μm and less than 250 μm.

Therefore, the laser shaving device is able to reduce the length of the hair by at least 100 μm in one stroke.

The optical system may adjust said laser beam to said cutting distance which is greater than 150 μm and less than 200 μm.

The optimal laser-skin distance between 150 μm and 200 μm allows the laser shaving device to reduce the length of the hair the most in one stroke.

Therefore, the user is able to control his own shaving ritual and vary the length of stubble it depending on the occasion. It removes the need for multiple devices or interchangeable heads.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
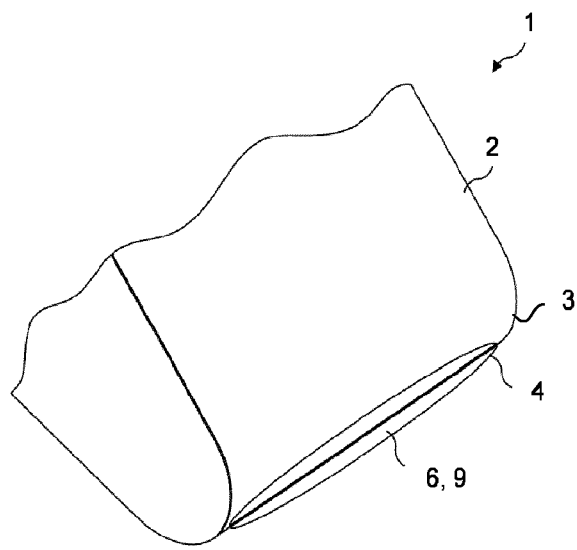
FIG. 1 shows a perspective view of the recess and of a laser shaving device for cutting hair using a laser beam.
Figure 2:
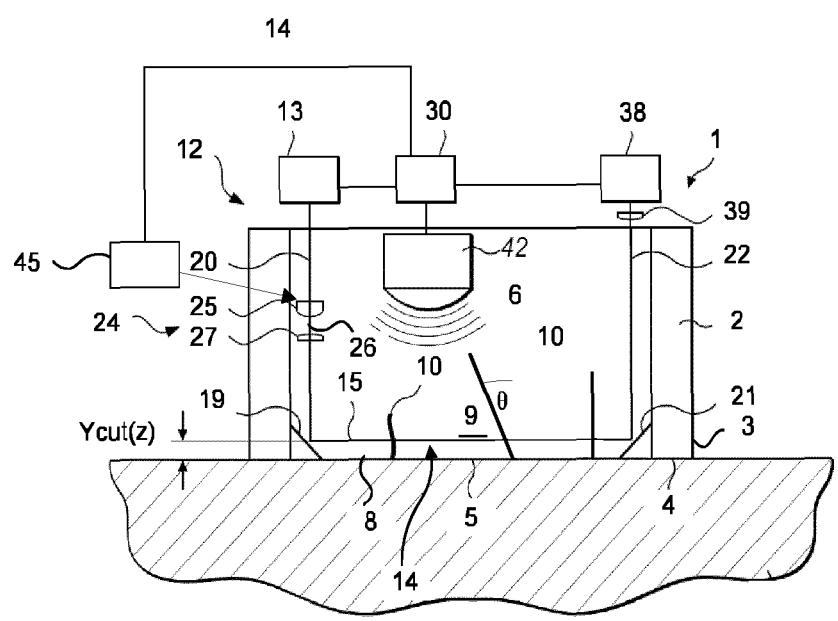
FIG. 2 shows a front view schematic diagram of the recess end of the laser shaving device of FIG. 1.

As shown in FIG. 1 and FIG. 2, a laser shaving device 1 for cutting hair comprises a housing 2. The housing 2 may comprise a guard 3. The guard 3 may be a hair and skin manipulation module. The housing 2 has a skin engaging face 4. The skin engaging face 4 is placed against a skin surface 5. The skin surface 5 may be, for example, but not limited to, the face or leg of a user or person being treated.

The skin engaging face 4 comprises a recess 6. In the present embodiment, the centre of the recess 6 is concentric with the centre of the skin engaging face 4. The recess 6 has a substantially oval cross-section. However, it will be understood that the shape of the cross-section is not limited thereto. For example, the cross-section of the recess 6 may be rectangular.

The recess 6 is a slit. The recess 6 is greater than or equal to 0.3 mm and less than or equal to 2 mm wide in the direction of the shaving stroke. Preferably, the recess width is greater than 0.3 mm and less than 1.5 mm. The recess width helps to control the doming of the skin surface 5. In the present embodiment, the width of the recess 6 is 0.8 mm. The width of the recess 6 in the present embodiment helps to position the skin surface for cutting a typical 1 or 2 day beard. The length of the recess 6 in the direction perpendicular to the shaving stroke may be determined by the size of the laser shaving device 1 but preferably in the range of 10 mm to 40 mm. In the present embodiment, the length of the recess 6 is 35 mm.

In the present embodiment, the skin engaging face 4 lies in a plane 8 that extends across the recess 6. The plane 8 extends generally perpendicular to the longitudinal axis of the housing 2 of the laser shaving device 1. However, it will be understood that for ergonomic reasons the angle between the plane 8 and the longitudinal axis of the housing 2 may vary.

The recess 6 comprises a cutting zone 9. When the skin engaging face 4 of the laser shaving device 1 is placed against a skin surface 5 and moved along it, hairs 10 protruding from the skin surface 5 extend into the cutting zone 9 in the recess 6.

The housing 2 of the laser shaving device 1 comprises an optical system 12. The optical system 12 is located within the housing 2. The optical system 12 comprises a laser beam generator 13. The laser beam generator 13 may be for example, but not limited to, a laser diode. The laser beam generator 13 is configured to generate a laser beam 14. The laser beam 14 is used to cut hairs 10 which extend into the cutting zone 9 by evaporation due to optical absorption.

The optical system 12 directs the laser beam 14 across the recess 6 so that it is parallel to and spaced from the plane 8 of the recess 6 on which the skin engaging face 4 lies. The housing 2, or more specifically, the guard 3, mechanically spaces the laser beam 14 from the skin surface 5. The section of the laser beam 14 which is parallel to the skin engaging face 4 is a cutting section 15 of the laser beam 14. The optical system 12 directs the laser beam 14 such that it extends across the recess 6 proximate to the plane 8. The point at which the cutting section 15 of the laser beam 14 travels across the recess 6 is the cutting zone 9.

In this way, when the skin engaging face 4 of the housing 2 is placed against the skin surface 5, the cutting section 15 of the laser beam 14 is substantially parallel to and spaced from the skin surface 5.

In the present embodiment, the laser beam 14 emitted by the laser beam generator 13 is initially directed downwards towards the skin surface 5. The optical system 12 redirects the laser beam 14 along the desired optical path.

The optical system 12 comprises a first reflective element 19. The first reflective element 19 is positioned on one side of the cutting zone 9. The first reflective element 19 is configured to reflect an incident section 20 of the cutting section 15 of the laser beam 14 across the cutting zone 9 of the recess 6. That is, the first reflective element 19 is configured to reflect the incident section 20 of the cutting section 15 of the laser beam 14 across the cutting zone 9, such that the cutting section 15 of the laser beam 14 follows a path which is substantially parallel to and spaced from the plane 8 that extends across the recess 6 of the laser shaving device 1.

The optical system 12 further comprises a second reflective element 21. The second reflective element 21 is positioned on an opposite side of the cutting zone 9 to the first reflective element 19. The second reflective element 21 is configured to reflect the cutting section 15 of the laser beam 14 away from the cutting zone 9. The second reflective element 21 is configured to reflect the cutting section 15 of the laser beam 14 away from the skin surface 5. The section of the laser beam 14 reflected by the second reflective element 21 is a 'used' section 22 of the laser beam 14. The 'used' section 22 of the laser beam 14 may be directed towards an energy dissipater (not shown) so that it does not interact with the skin surface 5 or another part of the laser shaving device 1.

In the embodiment shown in FIG. 2, the incident section 20 of the laser beam 14 which is incident on the first reflective element 19 is perpendicular to the plane 8 extending across the recess 6 of the housing 2. The first reflective element 19 reflects the incident section 20 of the laser beam 14 through 90 degrees such that the cutting section 15 of the laser beam 14 is parallel to the plane 8 extending across the recess 6. The second reflective element 21 is configured to reflect the cutting section 15 of the laser beam 14 through 90 degrees such that the 'used' section 22 of the laser beam 14 extends perpendicularly away from the plane 8 extending across the recess 6.

However, it will be appreciated that the first and second reflective elements 19, 21 may be orientated differently or have different reflective angles depending on the position and orientation of the other parts of the optical system 12, such as the laser beam generator 13 and the energy dissipater (not shown).

Furthermore, it will be appreciated that the first and second reflective elements 19, 21 may not be located at a side of the cutting zone 9 of FIG. 1 and FIG. 2. They may alternatively be located anywhere within the recess 6, depending on the position, orientation and configuration of the other components of the optical system 12. The first and second reflective elements 19, 21 may be omitted.

However, the cutting section 15 of the laser beam 14 should remain substantially parallel to the plane 8 extending across the recess 6 on which the skin engaging face 4 lies so that the distance between the skin engaging face 4 and the cutting section 15 of the laser beam 14 is substantially constant across the cutting zone 9 in the recess 6. Therefore, the cutting section 15 of the laser beam 14 will be prevented from irritating the skin surface 5 on one side of the cutting zone 9 and not cutting hair 10 short enough on the other.

The first and second reflective elements 19, 21 may comprise a mirror or a prism or any other optically reflective surface. Furthermore, the invention is not limited to two reflective elements.

The optical system 12 of the laser shaving device 1 further comprises a lens arrangement 24. The lens arrangement 24 is configured to focus the laser beam 14 emitted from the laser beam generator 13. In the present embodiment, as shown in FIG. 2, the lens arrangement 24 comprises a collimating lens 25. The laser beam 14 emitted from the laser beam generator 13 is directed towards the collimating lens 25. The collimating lens 25 reduces or eliminates the divergence of the laser beam 14. The collimating lens 25 of the optical system 12 produces a collimated section 26 of the laser beam 14. The collimated section 26 of the laser beam 14 is directed towards the first reflective element 19.

The lens arrangement 24 of the optical system 12 further comprises at least one focus lens 27. The focus lens 27 causes the collimated section 26 of the laser beam 14 to converge forming a converging incident section 20 of the laser beam 14. Alternatively, a plurality of focus lenses 27 can be used. The focus point of the cutting section 15 of the laser beam 14 is in the middle of the shaving width which corresponds to the axis of the recess 6. In one embodiment, the focus lenses 27 can produce a more intense collimated section 26 of the laser beam 14.

Figure 3:
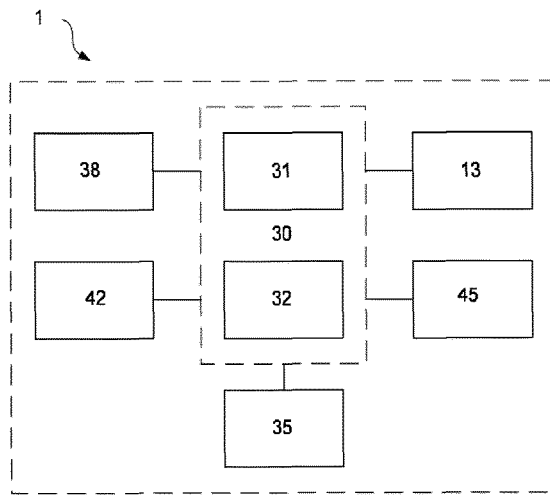
FIG. 3 shows a schematic block circuit diagram of the laser shaving device of FIG. 2.

The laser shaving device 1 further comprises a controller 30. The controller 30 is configured to control the operation of the laser beam generator 13. Therefore, the controller 30 controls the operation of the cutting section 15 of the laser beam 14. Referring to FIG. 3, the controller 30 comprises a processor 31. The controller 30 further comprises a memory 32. The controller 30 is able to operate the optical system 12.

The processor 31 may take any suitable form. For instance, the processor 31 may be or include a microcontroller, plural microcontrollers, circuitry, a single processor, or plural processors. The controller 30 may be formed of one or multiple modules.

The memory 32 may take any suitable form. The memory 32 may include a non-volatile memory and/or RAM. The non-volatile memory may include read only memory (ROM), a hard disk drive (HDD) or a solid state drive (SSD). The memory stores, amongst other things, an operating system. The memory may be disposed remotely. The RAM is used by the processor 31 for the temporary storage of data.

The operating system may contain code which, when executed by the controller 30, controls the operation of each of the hardware components in the laser shaving device 1. The controller 30 may be able to cause one or more objects, such as one or more profiles, to be stored remotely or locally by the memory 32. The controller 30 may be able to refer to one or more objects, such as one or more profiles, stored by the non-volatile memory and upload the one or more stored objects to the RAM.

The controller 30 is operable to operate the laser shaving device in response to an input, for example a user input 35. The controller 30 is configured to operate the optical system 12.

The user input 35 comprises some form of user interface. Optionally, the laser shaving device 1 includes controls and/or displays for adjusting an operating characteristic of the laser shaving device 1, such as the power. The user input 35 allows a user to operate the laser shaving device 1, for example to turn the laser shaving device 1 on and off. The user input 35 may, for example, be a button, touch screen or switch.

Other components that the laser shaving device 1 may comprise, which are not shown, may include other optical components such as a filter or windows to limit the passage of detritus in the laser shaving device 1. Other components necessary for the operation of the laser shaving device 1 may also be located within the housing 2, such as a battery or a connection to an external power cable (not shown). Moreover, the housing 2 of the laser shaving device 1 may also comprise a handle and any switches, buttons or other controls and displays necessary to operate the laser shaving device 1, which may form the user input 35.

In the present embodiment, the laser shaving device 1 is provided with a laser beam sensor 38. The laser beam sensor 38 may be an electronic sensor. The laser beam sensor 38 is configured to generate information indicative of one or more optical properties of the laser beam 14 when the optical system 12 is operated. The information generated by the laser beam sensor 38 is provided to the controller 30. The controller 30 may control the operation of one or more components of the optical system 12 in dependence on the information provided by the laser beam sensor 38.

Alternatively, the laser beam sensor 38 may be a photodiode array. The laser beam sensor 38 is disposed at the end of the optical path of the laser beam 14. In the present embodiment, the laser beam sensor 38 is at the energy dissipater (not shown). However, it will be understood that alternative sensor arrangements may be used.

The laser beam sensor 38 is configured to detect one or more optical properties of the laser beam 14. A detector lens 39 is disposed on the optical path of the laser beam 14 prior to the laser beam sensor 38. The detector lens 39 is configured to adjust the dimensions of the laser beam 14 to suit the laser beam sensor 38. For example, the detector lens 39 may be configured to ensure that the dimensions of the laser beam 14 at the laser beam sensor 38 correspond to the resolution of the laser beam sensor 38. The detector lens 39 may be omitted.

The laser beam sensor 38 intersects the optical path of the laser beam 14. The laser beam sensor 38 is configured to determine one or more properties of the laser beam 14. For example, the laser beam sensor 38 may be configured to determine the position of the laser beam 14 and/or the intensity of the laser beam 14.

When the laser beam sensor 38 is configured to provide information on the position of the laser beam 14, the laser beam sensor 38 is configured to generate information on the position at which the 'used' section 22 of the laser beam 14 intersects the laser beam sensor 38. The controller 30 is able to determine the position of the cutting section 15 of the laser beam 14 relative to the plane 8 of the recess 6.

When the laser beam sensor 38 is configured to provide information on the intensity of the laser beam 14, the laser beam sensor 38 is configured to generate information on the intensity of the laser beam 14 intersecting the laser beam sensor 38. In the present arrangement that is at the end of the optical path of the laser beam 14.

Figure 4:
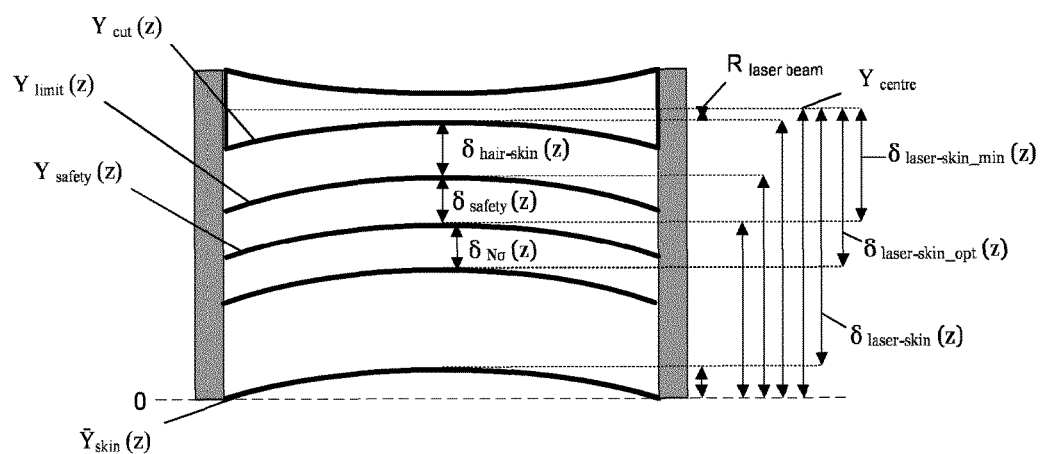
FIG. 4 shows a schematic diagram of an optimum distance between the laser beam and a skin surface.

In the present invention, the laser beam sensor 38 is configured to generate information indicative of the position of the laser beam 14. The controller 30 uses the information generated by the laser beam sensor 38 to determine the distance of the centre of the cutting section 15 of the laser beam 14 from the skin engaging face 4. Referring to FIG. 4, the vertical distance from the plane 8 of the recess 6 to centre of the cutting section 15 of the laser beam 14 is a centre beam height $Y_{centre}$.

The laser beam 14 has a Gaussian profile. That is, the maximum intensity of the laser beam 14 is at its centre, the centre beam height $Y_{centre}$. The controller 30 can calculate the radial variation in the intensity of the laser beam 14 based on the given power or energy of the laser beam 14, the orientation of the components of the optical system 12 and the information generated by the laser beam sensor 38. In one embodiment, the power or energy of the laser beam 14 may be controlled by the user input 35.

Due to the focusing of the laser beam 14 to increase its maximum intensity, the upper and lower edges of the laser beam 14 will vary vertically in distance from the plane 8 that extends across the recess 6 as the laser beam 14 travels across the recess 6. The lower and upper edges of the laser beam 14 are vertically above the centreline of the plane 8 that extends across the recess 6.

The edges will converge as they travel towards the focus point in the middle of the cutting zone 9 where the laser beam 14 is at its peak intensity. The edges of the laser beam 14 diverge as they travel away from the focus point. Therefore, the controller 30 can calculate the intensity and position of the cutting section 15 of the laser beam 14 at all points within the recess 6.

Alternatively, the laser beam sensor 38 may be configured to generate information indicative of both the position of the laser beam 14 and the intensity of the laser beam 14. Therefore, the controller 30 is provided information indicative of the intensity of the cutting section 15 of the laser beam 14 over a range of distances from the plane 8 of the recess 6.

In the present embodiment, the laser beam sensor 38 is configured to generate information indicative of a laser beam cutting height $Y_{cut}(z)$. The laser beam cutting height $Y_{cut}(z)$ defines the minimum distance from the plane 8 that extends across the recess 6 at which a hair 10 is cut. The laser beam cutting height $Y_{cut}(z)$ is the distance from the centreline of the plane 8 to a lower edge of a circumference defined by a radius of the cutting section 15 of the laser beam 14 which has an intensity large enough to cut hair 10.

Therefore, the cutting section 15 of the laser beam 14 comprises a cutting radius $R_{cut}(z)$. The cutting radius $R_{cut}(z)$ is defined as the difference between the centre beam distance $Y_{centre}$ and the laser beam cutting height $Y_{cut}(z)$, also shown in FIG. 4 by reference $\delta_{cut}(z)$.

Furthermore, the laser beam sensor 38 is configured to generate information indicative of an allowable intensity laser beam height $Y_{limit}(z)$. The allowable intensity laser beam height $Y_{limit}(z)$ defines the maximum distance from the plane 8 that extends across the recess 6 at which the skin surface 5 will not be harmed by the laser beam 14. The allowable intensity laser beam height $Y_{limit}(z)$ is the distance from the centreline of the plane 8 to a lower edge of a circumference defined by a radius of the cutting section 15 of the laser beam 14 which has a maximum allowable intensity without causing damage to the skin surface 5.

Therefore, the cutting section 15 of the laser beam 14 further comprises an allowable intensity radius $R_{limit}(z)$. The allowable intensity radius $R_{limit}(z)$ is defined as the difference between the centre beam distance $Y_{centre}$ and the allowable intensity laser beam height $Y_{limit}(z)$. The distance between the laser beam cutting height $Y_{cut}(z)$ and the allowable intensity laser beam height $Y_{limit}(z)$ is the minimum laser-skin distance $\delta_{hair-skin}(z)$.

$$\delta_{hair-skin}(z) = Y_{cut}(z) - Y_{limit}(z)$$

The laser beam sensor 38 is configured to provide information indicative of the distance between the various heights of parts of the cutting section 15 of the laser beam 14 and the reference position. In the present embodiment, the reference position is based on the plane 8 that extends across the recess 6 of the laser shaving device 1, especially the centreline of the plane 8 which is vertically below the lowest edges of the various parts of the cutting section 15 of the laser beam 14. Therefore, the provided information indicative of the various heights of the cutting section 15 of the laser beam 14 and the reference position are the perpendicular distances. However, it will be understood that an alternative reference position may be used. For example, the reference position may be a neutral calibrated position of the cutting section 15 of the laser beam 14.

The laser shaving device 1 further comprises a skin surface sensor 42. The skin surface sensor 42 is configured to generate information indicative of the distance between the skin surface 5 in the recess 6 and the plane 8 that extends across the recess 6 when the laser shaving device 1 is positioned against the skin surface 5.

The distance measured by the skin surface sensor 42 is the skin height. However, although the skin surface 5 is in contact with the skin engaging face 4, the skin surface 5 proximate the plane 8 that extends across the recess 6 extends into the recess 6. This is known as skin doming. Therefore, the skin surface sensor 42 measures a skin doming height $\overline{Y}_{skin}(z)$. The skin doming height $\overline{Y}_{skin}(z)$, shown in FIG. 4, is the mean line of the skin surface 5. The skin doming height $\overline{Y}_{skin}(z)$ is an ideal skin surface that would be present if the skin surface 5 was averaged out to be smooth. The skin surface 5 has a natural variation and therefore, the height of the skin surface 5 may vary relative to the skin doming height $\overline{Y}_{skin}(z)$.

Skin doming is exaggerated when the skin engaging face 4 is pushed into the skin surface 5 and/or the laser shaving device 1 is dragged across the skin surface 5. Because the skin surface 5 is constrained by the skin engaging face 4, the skin doming is usually largest towards the centre of the recess 6. Therefore, the skin doming height $\overline{Y}_{skin}(z)$ usually has a Gaussian profile.

The Gaussian profile of the skin doming height $\overline{Y}_{skin}(z)$ is dependent on the average skin doming height $\mu_{skin}$ and standard deviation of the skin doming height $\sigma_{skin}$. The guard 3 and recess 6 can control the average skin doming height $\mu_{skin}$ and standard deviation of the skin doming height $\sigma_{skin}$. The average skin doming height $\mu_{skin}$ can be kept below 100 μm. The standard deviation of the skin doming height $\sigma_{skin}$ can be controlled within 20 to 50 μm. The information generated by the skin surface sensor 42 indicative of the skin doming distance is provided to the controller 30 which controls operation of the laser beam generator 13.

The skin surface sensor 42 may be, for example, an electronic sensor which is configured to generate information indicative of the distance between the skin surface 5 in the recess 6 and the plane 8 that extends across the recess 6 when the laser shaving device 1 is positioned against the skin surface 5.

The skin surface sensor 42 may be an optical sensor, such as a confocal lens which uses optical measuring techniques and does not need to contact the skin surface 5 to measure the distance between the skin surface 5 and the plane 8 that extends across the recess 6 of the laser shaving device 1. The skin surface sensor 42 may be configured to generate information indicative of the position of the skin surface 5 by, for example, triangulation measurement, scattered light measurement and/or shadow measurement.

The provided information indicative of the distance between the skin surface 5 in the recess 6 and the plane 8 that extends across the recess 6 is the perpendicular distance. However, it will be understood that an alternative reference position may be used. For example, the reference position may be a neutral calibrated position of the cutting section 15 of the laser beam 14 or the ideal skin surface that would be present if the skin surface 5 was averaged out to be smooth.

The skin surface sensor 42 is disposed in the recess 6 of the housing 2. The skin surface sensor 42 is a non-contact skin distance sensor. That is, the skin surface sensor 42 is configured to measure the distance between the skin surface 5 in the recess 6 and the plane 8 that extends across the recess 6, when the laser shaving device 1 is positioned against the skin surface 5. The skin surface sensor 42 may be a reflective or transmissive optical sensor. The skin surface sensor 42 may use one or more wavelengths of light in the visible and/or near infra-red radiation regions. However, it will be understood that alternative sensor arrangements may be used.

The skin surface sensor 42 comprises a light source (not shown) and a detector (not shown). A light path is defined between the light source and the detector. The skin surface 5 forms part of the light path when it is disposed at the plane 8 that extends across the recess 6. When the skin surface 5 is disposed at the plane 8 that extends across the recess 6, the recess 6 is enclosed.

Although in the present arrangement the skin surface sensor 42 is disposed in the recess 6 and is configured to detect the skin surface 5 positioned relative to the plane 8 that extends across the recess 6, it will be understood that in an alternative embodiment the skin surface sensor 42 may be disposed in another position.

The controller 30 is configured to refer to the information generated by the laser beam sensor 38 indicative of the distance between the allowable intensity radius $R_{limit}(z)$ of the cutting section 15 of the laser beam 14 and the plane 8 that extends across the recess 6. The controller 30 is configured to refer to the information generated by the skin surface sensor 42 indicative of the skin doming distance $\overline{Y}(z)$, i.e. the distance between skin surface 5 in the recess 6 and the plane 8 that extends across the recess 6 when the laser shaving device 1 is positioned against the skin surface 5. In the present embodiment, the reference positions are the same. However, in an alternative embodiment, the reference positions may be different with a known spacing.

Based on the information generated by the laser beam sensor 38 and the skin surface sensor 42, the controller 30 is able to generate information indicative of the distance between the allowable intensity radius $R_{limit}(z)$ of the cutting section 15 of the laser beam 14 and the skin doming of the skin surface 5 across the width of the recess 6.

However, due to the natural variation of the skin surface 5 which has domed into the recess 6 and laser beam instability, the allowable intensity laser beam height $Y_{limit}(z)$ can vary. This results in a range of uncertainty in which the exact position of the allowable intensity radius $R_{limit}(z)$ from the centreline $Y_{centre}$ of Y the laser beam 14 can not be determined.

Therefore, in order to prevent the skin surface 5 from becoming irritated by Therefore, the high intensity laser beam 14 above the varying allowable intensity laser beam distance $Y_{limit}(z)$, a laser beam safety height $Y_{safety}(z)$ is determined by the controller 30. The controller 30 determines the laser beam safety height $Y_{safety}(z)$ by subtracting a safety distance $\delta_{safety}(z)$ from the allowable intensity laser beam height $Y_{limit}(z)$. The safety distance $\delta_{safety}(z)$ may be, for example, but not limited to, a percentage of the allowable intensity laser beam radius $R_{limit}(z)$ or an arbitrary distance.

The controller 30 monitors the information generated by the skin surface sensor 42 indicative of the skin doming height $\overline{Y}_{skin}(z)$ and compares it to the calculated laser beam safety height $Y_{safety}(z)$. In the event that the skin doming height $\overline{Y}_{skin}(z)$ exceeds the laser beam safety height $Y_{safety}(z)$, the controller 30 is configured to deactivate the laser beam generator 13. This removes the chance of the skin surface 5 being damaged by a part of the cutting section 15 of the laser beam 14 with too high an intensity.

The closeness of a single hair 10 is governed by the distance between the laser beam cutting height $Y_{cut}(z)$ and skin doming height $\overline{Y}_{skin}(z)$. The closer the two heights, the shorter the cut hair length $L_{stubble\_cut}$. The cut hair length is also dependent on the angle, θ, shown in FIG. 2, that the hair extends into the recess 6 relative to the vertical and the hair lift $\delta_{lift}$. For simplicity of the description both θ and $\delta_{lift}$ are assumed to be zero.

$$L_{Stubble}(z) = ((Y_{cut}(z) - \overline{Y}_{skin}(z))/\cos\theta) - \delta_{lift}$$

if $\overline{Y}_{skin}(z) < Y_{limit}(z) - \delta_{safety}(z)$ and $Y_{top} > Y_{cut}(z)$ In order to achieve the closest shave possible, the lower edge of the cutting section 15 of the laser beam 14 must be placed as close to the skin surface 5 as possible. The minimum distance between the laser beam cutting height $Y_{cut}(z)$ and the laser beam safety height $Y_{safety}(z)$ is the sum of the minimum laser-skin distance $\delta_{hair-skin}(z)$ and the safety distance $\delta_{safety}(z)$. This distance is also known as the optical baseline distance (OBD) of the optical system 12.

$$Y_{cut}(z) - Y_{safety}(z) = \delta_{hair-skin}(z) + \delta_{safety}(z) = OBD$$

Therefore, the controller 30 can calculate the minimum distance between the lower edge of laser beam 14 with intensity high enough to cut hair and the skin surface 5 in dependence on the information generated by the laser beam sensor 38. In reality, the minimum possible stubble length $L_{Stubble\_min}(z)$ is dependent on the OBD and the angle that the hair 10 extends to a plane extending perpendicularly from the plane 8 of the recess 6.

The hair 10 will only be cut when the skin doming height $\overline{Y}_{skin}(z)$ does not exceed the laser beam safety height $Y_{safety}(z)$ and the hair 10 extends further into the recess than the laser beam cutting height $Y_{cut}(z)$. As previously explained, the distance between the laser beam cutting height $Y_{cut}(z)$ and the skin doming height $\overline{Y}_{skin}(z)$ is the Optical Baseline Distance (OBD).

$$L_{Stubble}(z)=((Y_{cut}(z)-\overline{Y}_{skin}(z))/\cos\theta)-\delta_{lift}=(OBD/\cos\theta)-\delta_{lift}$$

Knowing the calculation for the length $L_{Stubble}(z)$ of a hair 10 and assuming that the skin doming height $\overline{Y}_{skin}(z)$ is described by a Gaussian distribution, the length $L_{Stubble}(z)$ of a hair 10 can be given by the laser beam cutting height $Y_{cut}(z)$ minus the height y of the skin surface 5 at a particular point when the laser beam 14 is on and the original length $L_{Uncut}$ when the laser beam is off. Furthermore, the probability of each outcome can be determined.

$$L_{Stubble}=p_s(Y<Y_{safety}(z))((Y_{cut}(z)-y)+p_s(y>Y_{safety}(z))(L_{Uncut})$$

This can be applied to a stroke of the laser shaving device 1 along the skin surface 5 and an expression for the average length of the hair $L_{Av\ stubble}$ can be obtained.

$$L_{av\ stubble}=p_s(y<Y_{safety}(z))((Y_{cut}(z)-\mu_{skin})+p_s(y>Y_{safety}(z))(L_{Uncut})$$

Furthermore, the controller 30 can determine the cutting radius $R_{cut}(z)$ of the laser beam 14. Consequently, a minimum allowable distance $\delta_{laser-skin\_min}(z)$ between the centreline $Y_{centre}$ of the laser beam 14 and the skin surface 5 can be determined by the controller 30 in dependence on the information generated by the laser beam sensor 38.

The minimum allowable distance $\delta_{laser-skin\_min}(z)$ gives the closest shave possible which results in the shortest length of stubble $L_{Stubble\_min}(z)$ possible. If the user tries to cut the hair 10 to a length which is shorter than the OBD then the controller 30 will deactivate the laser beam generator 13 because the skin surface 5 will exceed the laser beam safety height $Y_{safety}(z)$. Therefore, the minimum allowable distance $\delta_{laser-skin\_min}(z)$ is a laser beam deactivation threshold.

$$\delta_{laser-skin\_min}(z)=R_{cut}(z)+\delta_{hair-skin}(z)+\delta_{safety}(z)$$

However, when the cutting section 15 of the laser beam 14 is configured such that the average skin doming distance $\overline{Y}_{skin}(z)$ is equal or close to the laser beam safety height $Y_{safety}(z)$, the laser beam 14 will be deactivated because the variations in the skin surface 5 will often exceed the laser beam safety height $Y_{safety}(z)$. Therefore, the minimum possible stubble length $L_{Stubble\_min}(z)$ can only be achieved after a larger number of strokes. Assuming that a user can perform an unlimited number of strokes, for a given OBD, the laser shaving device 1 will eventually obtain the minimum possible stubble length $L_{Stubble\_min}(z)$ as an average length. However, an unlimited number of strokes is unacceptable for a normal shaving ritual.

Therefore, to accommodate a normal shaving ritual, the closeness of the shave must be compromised to decrease the number of strokes it takes to achieve an average closeness. In a normal shaving ritual, the number of strokes is generally limited to between 7 and 10. Therefore, an average cut stubble length $L_{Stubble\_cut}(z)$ will not attain the minimum possible stubble length $L_{Stubble\_min}(z)$ as an average length after 10 strokes. However, it is possible to obtain an acceptable average cut stubble length $L_{Stubble\_cut}(z)$ in a limited number of strokes by positioning the skin surface 5 at a specified position below the laser beam safety height $Y_{safety}(z)$.

In order for a shaving stroke to be considered acceptable, the laser beam 14 must be activated for at least a certain percentage of the time during the stroke. To achieve the desired percentage of laser beam activation time during a stroke, the probability that the skin position y is lower than or equal to the laser beam safety height $Y_{safety}(z)$ must be larger than or equal to the desired percentage.

$$p_s(y<Y_{safety}(z))>X$$

Therefore, in order for the laser beam to be activated for the desired percentage of time during a stroke, the average skin doming height $\overline{Y}_{skin}(z)$ into the recess 6 must be a specific distance from the centreline $Y_{centre}$ of the laser beam 14. By being at the specific distance, the desired percentage is achieved and the average cut stubble length $L_{Stubble\_cut}(z)$ is kept as small as possible.

The desired percentage of laser beam activation time corresponds to a variance $N\sigma_{\overline{Y}skin}$ of the average skin doming height $\overline{Y}_{skin}(z)$. In the present embodiment, the average skin doming height $\overline{Y}_{skin}(z)$ is controlled by the guard 3 and size of the recess 6. The variance $\sigma_{\overline{Y}skin}$ of the average skin doming height $\overline{Y}_{skin}(z)$ is determined by the condition of the skin surface 5. The variance of the average doming height $\overline{Y}_{skin}(z)$ is a skin variation value σ which is indicative of the distance of the variation of the distance of the skin surface 5 from the average skin doming height $\overline{Y}_{skin}(z)$.

For the laser beam to be activated for a certain percentage of time, the distance between the average skin doming height $\overline{Y}_{skin}(z)$ and the laser beam safety height $Y_{safety}(z)$ must be such that that percentage of the skin surface 5 is below the laser beam safety height $Y_{safety}(z)$ during a stroke. Given the Gaussian profile of the skin doming height $\overline{Y}_{skin}(z)$ in the recess 6, the distance in terms of number of variances $N\sigma_{\overline{Y}skin}$ of the average doming height $\overline{Y}_{skin}(z)$ can be calculated from normal distribution tables. The number of variances $N\sigma_{\overline{Y}skin}$ of the average doming height $\overline{Y}_{skin}(z)$ gives a skin variation distance.

Therefore, an optimum laser-skin distance $\delta_{laser-skin\_opt}$ is dependent on the laser beam intensity, the safety distance $\delta_{safety}(z)$, the width of the recess 6 and the desired percentage of laser beam activation time of the laser shaving device 1. The laser-skin distance $\delta_{laser-skin\_opt}$ is a cutting distance at which the centreline $Y_{centre}$ of the laser beam 14 is positioned from the average skin doming height $\overline{Y}_{skin}(z)$.

$$\delta_{laser-skin\_opt}(z)=R_{cut}(z)+\delta_{hair-skin}(z)+\delta_{safety}(z)+N\sigma_{\overline{Y}skin}$$

For example, in one embodiment of the present invention, a stroke may be considered to be acceptable if the laser beam generator 13 is activated and generating the laser beam 14 for 75% of the time. For the probability that the skin surface 5 allows hair 10 to be cut to be 75% of the time, a variance in the average skin doming distance $\overline{Y}_{skin}(z)$ of roughly 0.7 $\sigma_{\overline{Y}skin}$ must be allowed. Therefore, the centreline $Y_{centre}$ of the laser beam 14 must be positioned such that the laser beam safety height $Y_{safety}(z)$ is placed above the average skin doming distance $\overline{Y}_{skin}(z)$ by roughly 70% of the skin doming spread $\sigma_{\overline{Y}skin}$.

Therefore, when the variance in the average skin doming distance $\overline{Y}_{skin}(z)$ is 75 μm, the optimum laser-skin distance $\delta_{laser-skin\_opt}(z)$ is in the range of 50-300 μm. This gives a first stroke efficiency of more than 80 μm. When the variance in the average skin doming distance $\overline{Y}_{skin}(z)$ is 50 μm, the optimum laser-skin distance $\delta_{laser-skin\_opt}(z)$ is in the range of 100-250 μm. This gives a first stroke efficiency of more than 100 μm. When the variance in the average skin doming distance $\overline{Y}_{skin}(z)$ is 25 μm, the optimum laser-skin distance $\delta_{laser\text{-}skin\_opt}$ is in the range of 150-200 μm. This gives the maximum efficiency for a first stroke.

In the embodiment described above, the laser shaving device 1 is configured to cut hair 10 to a predetermined constant average cut stubble length $L_{Stubble\_cut}(z)$ in 10 strokes. It will be understood, however, that various embodiments of the laser shaving device 1 will be configured to cut hair to different average cut stubble lengths $L_{Stubble\_cut}(z)$ in varying numbers of strokes.

In another embodiment, the laser shaving device 1 may comprise interchangeable cutting heads (not shown) or guards 3. The interchangeable cutting heads (not shown) or guards 3 may change the optimal distance of the laser shaving device 1 depending on the shaving ritual, strokes and average closeness, the user desires.

In a further embodiment, the laser shaving device 1 comprises an actuator 45. The actuator 45 is configured to act on one or more components of the optical system 12. The actuator 45 may be configured to rotate the at least one lens 24 or the first reflective element 19 to change the centre beam height $Y_{centre}$ or intensity of the cutting section 15 of the laser beam 14.

The actuator 45 may be an electronic actuator, for example a voice coil actuator, spindle motor with gear or a piezo electrical translator. The actuator 45 acts on one or more components of the optical system 12 based on commands from the controller 30.

In the present embodiment, the user input 35 is configured to allow the user to select the desired percentage of time that the laser beam 14 is activated during a stroke. Therefore, the laser shaving device 1 may be used to perform different shaving rituals depending on the desired closeness, number of strokes and time available.

For example, for a user limited by time, the number of strokes may be limited. Therefore, in order to achieve a close shave in the minimum number of strokes, the acceptable laser beam activation time may be higher, e.g. 84% of the stroke time. Therefore, a variance in the average skin doming distance $\overline{Y}_{skin}(z)$ of roughly $\sigma_{\overline{Y}skin}$ must be allowed for. The larger distance between the centreline $Y_{centre}$ of the laser beam 14 and the average skin doming distance $\overline{Y}_{skin}(z)$ means that the laser beam 14 is activated for a larger percentage of the time but that the length of the cut is longer.

Conversely, if the user is not limited by time, the user may select a lower percentage and use a larger number of strokes to achieve a closer shave. Therefore, the user has the freedom to tailor the shaving process to his needs depending on whether the speed of the shave in more important that the closeness, or vice versa. The user can input his preference via the user input 35 and the controller 30 of the laser shaving device 1 adjusts the optical system 12 via the actuator 45 to adopt the optimum laser-skin distance $\delta_{laser\text{-}skin\_opt}$.

In one embodiment, the average skin doming height $\overline{Y}_{skin}(z)$ and the variance $N\sigma_{\overline{Y}skin}$ of the average skin doming height $\overline{Y}_{skin}(z)$ may be determined by the controller 30 in dependence on information generated by the skin surface sensor 42 and the actuator 45 activated by the controller 30 to maintain the optimum distance from the skin surface 5 throughout the stroke.

It will be appreciated that the term "comprising" does not exclude other elements or steps and that the indefinite article "a" or "an" does not exclude a plurality. A single processor may fulfill the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A method for setting a cutting distance ($\delta_{laser\_skin\_opt}(z)$) between a laser beam and a skin surface in a laser shaving device, said laser shaving device having a laser deactivation threshold ($\delta_{laser\_skin\_min}(z)$),
   said method comprising:
   operating an optical system to generate the laser beam;
   determining a skin variation value ($\sigma$) indicative of the variation in the distance of the skin surface from a reference point;
   determining a cutting distance between said laser beam and the skin surface in dependence on at least the laser deactivation threshold and said skin variation value; and
   adjusting said optical system to locate the laser beam in dependence on said determined cutting distance,
   wherein determining said skin variation value comprises:
   generating information indicative of an ideal skin surface ($\overline{Y}_{skin}(z)$) and the distances from said ideal skin surface that said skin surface is; and
   determining a standard deviation of said skin surface distance from said ideal skin surface.

2. The method for setting the cutting distance between the laser beam and the skin surface in the laser shaving device according to claim 1, wherein determining said skin variation value further comprises:
   selecting a desired laser activation percentage during a shaving stroke corresponding to a shaving condition; and
   determining the corresponding percentage of said standard deviation that the skin variation distance must be in order to achieve said desired laser activation percentage.

3. The method for setting the cutting distance between the laser beam and the skin surface in the laser shaving device according to claim 1, wherein determining said laser beam deactivation threshold comprises generating information indicative of an allowable intensity radius $R_{limit}(z)$ of said laser beam and a safety margin distance $\delta_{safety}(z)$.

4. The method for setting the cutting distance between the laser beam and the skin surface in the laser shaving device according to claim 1, further comprising:
   generating information indicative of the distance between said laser beam and said skin surface; and
   ceasing generation of the laser beam when said skin surface has exceeded said laser beam deactivation threshold.

5. The method for setting the cutting distance between the laser beam and the skin surface in the laser shaving device according to claim 1, wherein said optical system adjusts said laser beam to be at said cutting distance, which is the sum of said laser beam deactivation threshold plus a skin variation distance ($\delta_{TNo}$), which is dependent on said skin variation value, from said skin surface.

6. The method for setting the cutting distance between the laser beam and the skin surface in the laser shaving device according to claim 5 wherein said skin variation distance is increased to reduce the number of shaving strokes needed to shave a beard and decreased to improve the closeness of the shave.

7. The method for setting the cutting distance between the laser beam and the skin surface in the laser shaving device according to claim 1, further comprising:
   selecting a desired shaving condition using a user input; and
   adjusting said optical system to position said laser beam at the corresponding cutting distance from said skin surface.

8. The method for setting the cutting distance between the laser beam and the skin surface in the laser shaving device according to claim 1, wherein said optical system adjusts said laser beam to said cutting distance which is greater than 50 μm and less than 300 μm.

9. The method for setting the cutting distance between the laser beam and the skin surface in the laser shaving device according to claim 1, wherein said optical system adjusts said laser beam to said cutting distance which is greater than 100 μm and less than 250 μm.

10. The method for setting the cutting distance between the laser beam and the skin surface in the laser shaving device according to claim 1, wherein said optical system adjusts said laser beam to said cutting distance which is greater than 150 μm and less than 200 μm.

\* \* \* \* \*